(12) United States Patent
Schewe et al.

(10) Patent No.: US 10,149,926 B2
(45) Date of Patent: Dec. 11, 2018

(54) HEMOSTATIC COMPOSITIONS AND METHODS OF MAKING AND USING SAME

(71) Applicant: BOSTON SCIENTIFIC SCIMED, INC., Maple Grove, MN (US)

(72) Inventors: Scott Schewe, Eden Prairie, MN (US); Robert Warner, Woodbury, MN (US); Jan Weber, Maastricht (NL); Michael Arney, Minneapolis, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 418 days.

(21) Appl. No.: 14/873,630

(22) Filed: Oct. 2, 2015

(65) Prior Publication Data

US 2016/0022880 A1 Jan. 28, 2016

Related U.S. Application Data

(63) Continuation of application No. 12/872,308, filed on Aug. 31, 2010, now abandoned.

(51) Int. Cl.
| | | |
|---|---|---|
| *A61B 17/00* | (2006.01) | |
| *A61L 31/12* | (2006.01) | |
| *A61K 9/70* | (2006.01) | |
| *A61L 15/44* | (2006.01) | |
| *A61L 15/62* | (2006.01) | |
| *A61L 31/04* | (2006.01) | |
| *A61L 31/14* | (2006.01) | |
| *A61L 31/16* | (2006.01) | |

(52) U.S. Cl.
CPC ........ *A61L 31/125* (2013.01); *A61B 17/0057* (2013.01); *A61K 9/70* (2013.01); *A61L 15/44* (2013.01); *A61L 15/62* (2013.01); *A61L 31/042* (2013.01); *A61L 31/148* (2013.01); *A61L 31/16* (2013.01); *A61B 2017/00004* (2013.01); *A61B 2017/00601* (2013.01); *A61B 2017/00654* (2013.01); *A61B 2017/00898* (2013.01); *A61L 2300/00* (2013.01); *A61L 2300/406* (2013.01); *A61L 2300/41* (2013.01); *A61L 2300/412* (2013.01); *A61L 2300/414* (2013.01); *A61L 2300/418* (2013.01); *A61L 2300/42* (2013.01); *A61L 2400/04* (2013.01)

(58) Field of Classification Search
CPC ...... A61B 17/0057; A61B 2017/00575; A61B 2017/00601; A61B 2017/0061; A61B 2017/00615; A61B 2017/00637; A61B 2017/00641; A61B 2017/00654; A61B 2017/00676; A61K 9/70; A61L 31/125
See application file for complete search history.

(56) References Cited

U.S. PATENT DOCUMENTS

| | | |
|---|---|---|
| 5,571,181 A | 11/1996 | Li |
| 2004/0001879 A1 | 1/2004 | Guo et al. |
| 2004/0005350 A1 | 1/2004 | Looney et al. |

(Continued)

FOREIGN PATENT DOCUMENTS

| | | |
|---|---|---|
| EP | 1 834 636 A1 | 9/2007 |
| WO | 2007/092350 A1 | 8/2007 |
| WO | 2008/083069 A2 | 7/2008 |

*Primary Examiner* — Dianne Dornbusch
(74) *Attorney, Agent, or Firm* — Seager, Tufte & Wickhem, LLP.

(57) ABSTRACT

The disclosure pertains to hemostatic compositions comprising a plurality of nonwoven fibers disposed in a rapidly soluble solid matrix and methods of making and using the same. The compositions may also comprise one or more therapeutic agents.

10 Claims, 1 Drawing Sheet

(56) References Cited

U.S. PATENT DOCUMENTS

| | | |
|---|---|---|
| 2004/0098023 A1 | 5/2004 | Lee et al. |
| 2005/0107826 A1 | 5/2005 | Zhu et al. |
| 2005/0123588 A1 | 6/2005 | Zhu et al. |
| 2005/0181015 A1 | 8/2005 | Zhong |
| 2006/0264130 A1 | 11/2006 | Karles et al. |
| 2007/0020228 A1 | 1/2007 | Williams |
| 2009/0148492 A1 | 6/2009 | Dave et al. |
| 2009/0171388 A1 | 7/2009 | Dave et al. |
| 2010/0256679 A1 | 10/2010 | Ducharme |

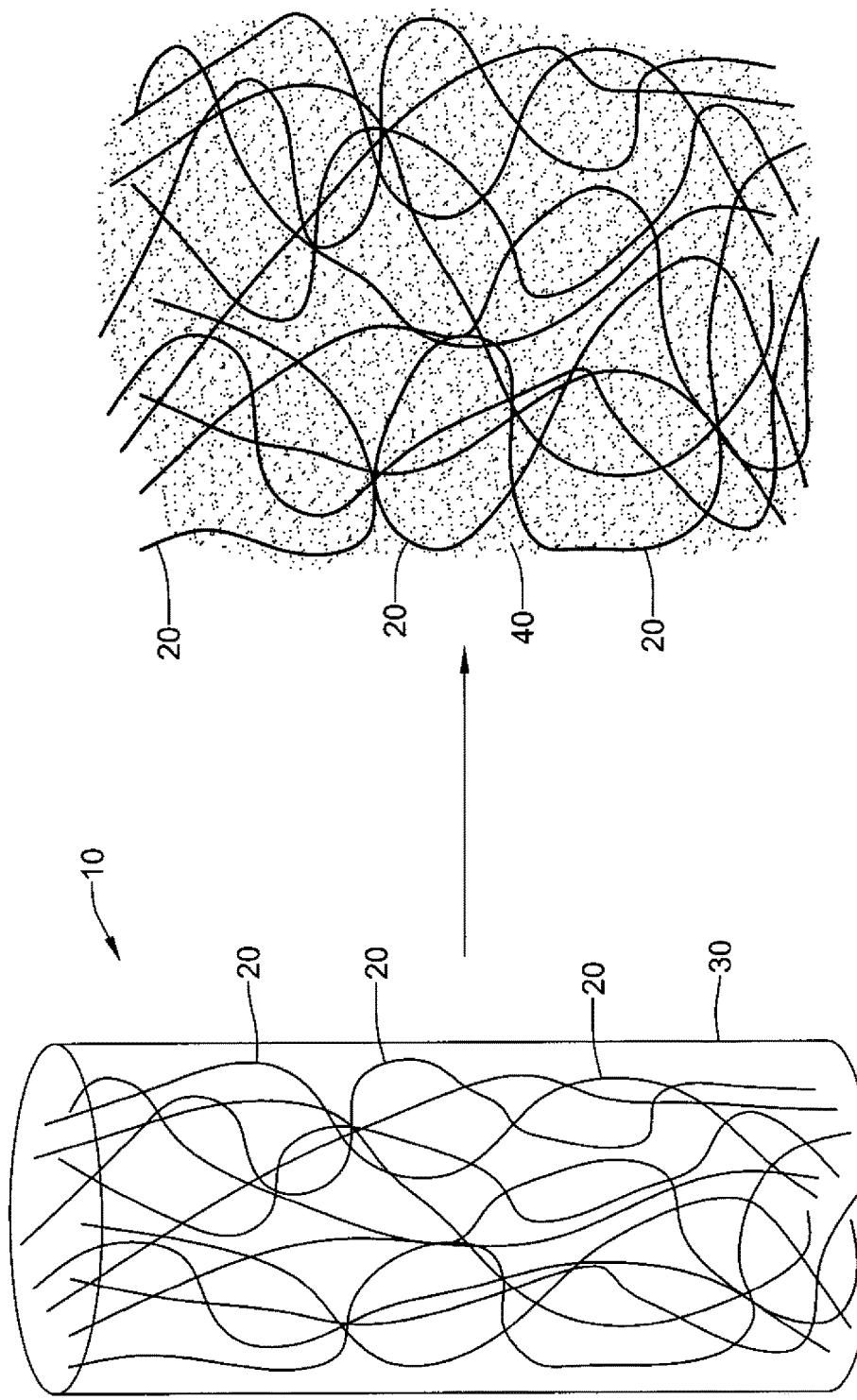

HEMOSTATIC COMPOSITIONS AND METHODS OF MAKING AND USING SAME

RELATED APPLICATIONS

This application is a continuation of U.S. patent application Ser. No. 12/872,308, filed Aug. 31, 2010, now abandoned.

BACKGROUND

Heart and vascular disease are major problems in the United States and throughout the world. Conditions such as atherosclerosis result in blood vessels becoming blocked or narrowed. This blockage can result in lack of oxygenation of the heart, which has significant consequences because the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire such that the balloon is positioned adjacent a stenotic lesion. The balloon is then inflated and the restriction of the vessel is opened. During an atherectomy procedure, the stenotic lesion may be mechanically cut away from the blood vessel wall using an atherectomy catheter.

The non-invasive medical procedures identified above typically gain access to the vasculature through an opening formed in the femoral artery. For obvious reasons, once the procedure is completed the opening in the femoral artery will need to be closed. This may include applying direct pressure at the wound site. Alternatively, a device may be used to assist in the closing of the artery.

A wide variety of medical devices have been developed for medical use, for example, use in non-invasive medical procedures. Some of these devices include devices for closing an opening in a body lumen such as the femoral artery. Closure devices for closing an opening in a body lumen may include a plug such as a collagen or gelatin sponge. These closure devices may be disposed within the body lumen. Although the plug or sponge may have served the purpose of containing bleeding adjacent to the vessel within the first few hours following surgery, it is desirable that such plugs or sponges initially have and maintain sufficient mechanical strength to withstand pressure and/or flexure of the wound site. For this reason, the plugs are frequently designed to dissolve and/or biodegrade more slowly to ensure that they continue to function during the post operative period.

Accordingly, it would be desirable to provide a plug having good initial mechanical properties, but which dissolves rapidly and controllably following sealing of the puncture. In addition to sealing vessel punctures, such hemostatic devices may be used to seal a variety of punctures and incisions, such as may be formed during biopsies and other procedures.

SUMMARY

This disclosure pertains to a hemostatic composition comprising a plurality of nonwoven fibers; a rapidly soluble solid matrix; and one or more therapeutic agents. The nonwoven fibers may comprise a polysaccharide, generally a non-cellulosic polysaccharide. The disclosure also pertains to methods of forming a hemostatic article comprising providing and compressing a plurality of nonwoven fibers; introducing the compressed fibers into a mold; introducing and solidifying a rapidly soluble matrix material into the mold; solidifying the rapidly soluble matrix material; and removing the hemostatic composition from the mold while maintaining the rapidly soluble matrix material in a solid state as well as a method of sealing a tissue puncture using the hemostatic composition, said method comprising introducing the hemostatic composition into a tissue puncture; exposing the hemostatic composition to a body fluid or saline, thereby liquefying the rapidly soluble solid matrix; and allowing the plurality of nonwoven fibers to swell.

BRIEF DESCRIPTION OF DRAWINGS

FIG. 1A schematically illustrates a first state "A" of an embodiment of the invention.

FIG. 1B schematically illustrates a second state "B" of an embodiment of the invention.

DETAILED DESCRIPTION

The following description should be read with reference to the drawings wherein like reference numerals indicate like elements throughout the several views. The drawings, which are not necessarily to scale, are not intended to limit the scope of the claimed invention. The detailed description and drawings illustrate example embodiments of the claimed invention.

All numbers are herein assumed to be modified by the term "about." The recitation of numerical ranges by endpoints includes all numbers subsumed within that range (e.g., 1 to 5 includes 1, 1.5, 2, 2.75, 3, 3.80, 4, and 5).

As used in this specification and the appended claims, the singular forms "a", "an", and "the" include the plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments whether or not explicitly described.

The disclosure pertains to hemostatic compositions comprising a plurality of nonwoven fibers disposed in a rapidly soluble solid matrix and methods of making and using the same. The compositions may be useful in the construction of articles for closing vascular punctures or other tissue tracts. The compositions may also comprise one or more therapeutic agents.

FIGS. 1A and 1B show schematically the transformation of an article 10, comprising a hemostatic composition of an embodiment of the present disclosure, from a first state "A" in which a plurality of nonwoven fibers 20 having certain properties are compressed and contained within a rapidly soluble matrix 30 to a second state "B" in which the rapidly soluble matrix 30 has been at least partially dissolved and the plurality of nonwoven fibers 20 have been released from their compressed state. It will be appreciated that "rapid solubility" is a relative term indicating that the matrix 30 dissolves or otherwise disperses at a rate which is greater than the rate at which the material of the fibers 20 dissolves leaving the fibers substantially intact. In some embodiments, the matrix 30 disperses following melting. Although only a few nonwoven fibers 20 are illustrated to represent the transformation without undue clutter, it will be appreciated that many more fibers will typically be present in the article 10. Similarly, additional components typically present in such compositions, such as one or more therapeutic agents, surfactants, lubricants, soluble covers, delivery system components, positioning elements, and the like have been omitted for clarity.

Second state "B", while representing the nonwoven fibers 20 in an expanded configuration does not attempt to depict each of the possible transitional states in which the rapidly soluble matrix 30 dissolves and is replaced by clot 40 and/or tissue growth from surrounding tissue as a wound heals, as the details of such replacement are both sufficiently well known and may vary somewhat depending upon a variety of factors related to nature of a tissue puncture.

The plurality of nonwoven fibers 20 can be selected to provide a high surface area that may promote both initial rapid swelling in response to exposure to bodily fluids and/or saline and to promote the biodegradation of the fibers 20 as the wound heals. In some embodiments, the desired surface area may be achieved by employing fibers 20 having a diameter greater than about 50 nanometers and less than about 20 microns. Such fibers 20 may be produced by a number of techniques known in the art including, but not limited to, electrospinning In addition, known techniques may be employed to impart a surface texture to the fibers 20 to further increase their surface area. In some embodiments, the fibers may include soluble components, e.g., therapeutic agents or lower molecular weight biodegradable species which dissolve more readily than the fiber material upon contact with bodily fluids and/or saline, thereby leaving a porous fiber structure when the soluble components dissolve or otherwise are removed from the fibers 20. The fiber diameter, composition, molecular weight of the components, degree of crosslinking, and the like may be varied to control the rate at which the fibers 20 dissolve or bioabsorb following the at least partial dissolution of the rapidly soluble matrix 30.

As illustrated in FIG. 1A, the individual fibers of the plurality of nonwoven fibers 20 are present in substantially isolated form within the soluble matrix 30. It will be appreciated that the individual fibers may also or alternatively be present as, for example, a twisted cord, a nonwoven mat or sheet, or other arrangements. In such embodiments, the individual fibers may remain discrete entities or they may be bonded at some or all of their points of mutual contact. While the plurality of fibers has been depicted as disposed within a relatively rapidly soluble solid matrix 30 such that the long axes of the plurality of fibers generally coincides with a long axis of the resulting article 10, it will be appreciated that other arrangements are contemplated. The individual fibers may be randomly oriented, helically oriented, radially oriented, or may assume some other orientation if desired.

In some embodiments, the plurality of nonwoven fibers 20 may comprise one or more polysaccharides such as pectin, acetylated pectin, hyaluronic acid and derivatives of thereof, and the like. In some embodiments, the pectin and/or acetylated pectin may be derived from sugar beets. In other embodiments, the polysaccharide may be a non-cellulosic polysaccharide. The plurality of nonwoven fibers 20 may also include fibers comprising other biodegradable polymers including, but not limited to, polyglycolide, polylactide, poly(lactide-co-glycolide), poly(r-caprolactone), poly(dioxanone), polycaprolactone, poly(3-hydroxybutyric acid), poly(3-hydroxybutyric acid-co-3-hydroxyvaleric acid), alginates, collagen, chitosan, gelatin, fibrinogen, elastin, polyethers, polyanhydrides, polyesters, polyorthoesters, polyphosphazenes, polyvinyl alcohol, polyvinylpyrrolidone, polytrimethylene carbonate, and the like. In addition, natural protein fibers such as cotton, silk and wool may also be used. Without wishing to be bound by theory, it is believed that polysaccharides are well suited to this application for the reason that they degrade non-enzymatically to simple sugars and so tend to avoid inflammation and possible infection.

As noted above, in embodiments in which the nonwoven fibers 20 comprise one or more polymers, for example, those polymers listed above, the nonwoven fibers 20 may be partially crosslinked with known crosslinking agents for such polymers to control the rate of dissolution and/or bioabsorption of the fibers once they are exposed to bodily fluids and/or saline. Useful methods of crosslinking can include, for example, the use of compounds of opposite charge, including calcium salts, chitosan, etc. The fibers 20 may also be chemically crosslinked with formaldehyde, gluteraldehyde, genipin, certain carbodiimides, and the like. Crosslinking may occur concurrently with fiber formation or may be induced in a later step.

The plurality of nonwoven fibers 20 may be compressed, for example, radially, prior to being surrounded by a rapidly soluble matrix 30. The matrix 30 may be a rapidly soluble solid such as a sugar, e.g., dextran, which is solid at body temperature, or it may be a material which is liquid at body temperature and solid at the temperature of delivery, e.g., ice delivered at or below 0.degree. C. Simple sugars and materials which melt below body temperature can be well suited to this application for the reason that they generally degrade or disperse non-enzymatically and thus tend to avoid inflammation.

Although the rapidly soluble matrix 30 may be positioned about the compressed nonwoven fibers 20 in a number of ways including, but not limited to, molding and extrusion, the following discussion will focus on molding for simplicity of illustration. One of ordinary skill in art will be able to adapt other processes to position a plurality of nonwoven fibers 20 within a rapidly soluble solid matrix 30. For the sake of illustration, the plurality of fibers may be compressed and placed in a mold of suitable volume and shape. For example, the mold cavity may be the cylindrical shape illustrated in FIG. 1A as first state "A", a flattened oval, a sphere, a rectangular envelope, a sheet, a sleeve, a disk, or other useful shape. The cavity may include protrusions and/or recesses to impart posts, ridges, barbs, and the like (not shown) which may assist in maintaining the initial position of the molded article 10 once it is inserted into a tissue puncture (not shown) such as a wound tract for an arteriotomy, a biopsy puncture, an incision, and the like. The mold may include inserts and/or inserted elements if desired. Such inserts may provide a lumen within the finished article 10, or may cause a desirable element such as a suture or anchor to become embedded in the article.

Once the plurality of nonwoven fibers 20 is positioned within the mold, the rapidly dissolvable matrix material may be introduced into the mold. The matrix material may be introduced as a liquid and subsequently allowed to solidify. Alternatively, it may be introduced as a powder and subsequently sintered or solvent welded to form a solid matrix 30. Other means of introducing and solidifying the matrix 30 are also contemplated. One or more therapeutic agents may be introduced into the mold prior to the solidifying step. Once the rapidly soluble matrix 30 is solidified, the article 10 may be removed from the mold. If necessary, the article 10 then may be stored in an environment which preserves it in a solid state until just prior to insertion into a tissue puncture to be sealed.

In some embodiments, the resulting molded article 10 may be relatively rigid and have a fixed shape, while in other embodiments the rapidly soluble solid matrix 30 may possess a degree of elasticity which admits of deformation. Such deformation may facilitate insertion and/or initial retention of the article 10 within the tissue puncture. Although the rapidly soluble matrix 30 of FIG. 1A has been illustrated as a continuous solid matrix, it will be appreciated that the matrix 30 may, if desired, possess a degree of porosity. The porosity may be present initially as a foamed matrix or may result upon exposure to a bodily fluid or saline if one or more components of the matrix are more rapidly soluble or dispersible than a continuous matrix phase.

In addition to the plurality of nonwoven fibers 20 and the rapidly soluble solid matrix 30, the composition of article 10 may include other components including one or more therapeutic agents. Non-limiting examples include heparin, thrombus enhancing agents, anti-inflammatory agents, antibiotics, growth factors, stem cells, and the like. These agents may be distributed within or on the plurality of nonwoven fibers 20, within or on other fibers, or within or on the rapidly soluble solid matrix 30. For example, a therapeutic agent may be disposed within the fibers as a consequence of the fiber manufacturing process, the therapeutic agent may be disposed as a coating on the fibers during the production of the fibers, as a coating subsequently applied to the fibers, or may be imbibed by the fibers from a suitable solution. Similarly, one or more therapeutic agents may be provided within or on the rapidly soluble matrix in a variety of ways. The therapeutic agents may be soluble in the material of the plurality of nonwoven fibers and/or matrix material or may form a discrete phase.

As mentioned herein, the article 10 containing the plurality of nonwoven fibers 20, a rapidly soluble solid matrix 30 and one or more therapeutic agents, may also include additional components such as surfactants, lubricants, soluble covers, delivery system components, positioning elements, and the like. Other components such as clays and other reinforcing agents also may be present within the matrix to modify the initial mechanical properties of the article 10 while maintaining the ability of the article to rapidly dissolve when exposed to body fluids and/or saline.

In use, the articles 10 described herein, may be inserted into a tissue puncture to be sealed and exposed to at least one of a body fluid or saline to liquefy the rapidly soluble solid matrix 30 allowing the plurality of nonwoven fibers 20 to swell, thereby occluding the tissue puncture and releasing at least some of the therapeutic agent(s). It will be appreciated that in those embodiments in which the rapidly soluble matrix 30 is a liquid at body temperature, the contribution of a body fluid or saline to the liquefaction process may be primarily that of ensuring initial thermal contact with the article 10, whereupon the liquid released by initial melting may be sufficient to continue the melting process. In such embodiments, the body fluids associated with the tissue surfaces within the puncture may suffice to initiate the liquefaction process.

Although the illustrative examples described above relate to a generally plug-shaped article to be inserted into a tissue puncture, a sheet form is also contemplated. In such an embodiment, the sheet may be applied to the surface of the tissue to be sealed.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

What is claimed:

1. A method of sealing a tissue puncture comprising:
   providing a hemostatic composition comprising:
      a plurality of nonwoven fibers;
      a rapidly soluble solid matrix,
      wherein the fibers are embedded within the rapidly soluble solid matrix such that the space occupied by the fibers is free of voids; and
      one or more therapeutic agents;
   inserting the hemostatic composition into a tissue puncture;
   exposing the hemostatic composition to at least one of a body fluid or saline;
   liquefying the rapidly soluble solid matrix upon contact with the at least one of a body fluid or saline and releasing the plurality of nonwoven fibers; and
   allowing the plurality of nonwoven fibers to swell upon contact with the at least one of a body fluid or saline, thereby occluding the tissue puncture.

2. The method of claim 1, wherein the plurality of nonwoven fibers are greater than about 50 nanometers in diameter and less than about 20 microns in diameter.

3. The method of claim 1, wherein the plurality of nonwoven fibers comprise a non-cellulosic polysaccharide.

4. The method of claim 1, wherein the liquefying step releases at least a portion of the one or more therapeutic agents.

5. The method of claim 1, wherein the rapidly soluble solid matrix comprises a sugar.

6. The method of claim 1, wherein the rapidly soluble solid matrix consists of a sugar.

7. The method of claim 1, wherein the rapidly soluble solid matrix comprises water ice.

8. The method of claim 1, wherein the rapidly soluble solid matrix consists of water ice.

9. The method of claim 1, wherein the material of the plurality of nonwoven fibers includes crosslinks.

10. The method of claim 1, wherein the material of the plurality of nonwoven fibers swells upon contact with at least one of a body fluid or saline.

* * * * *